(12) United States Patent
Liu et al.

(10) Patent No.: US 8,768,035 B2
(45) Date of Patent: Jul. 1, 2014

(54) X-RAY SYSTEM AND METHOD FOR PROCESSING IMAGE DATA

(75) Inventors: James Zhengshe Liu, Glenview, IL (US); Paul Richard Granfors, Berkeley, CA (US); Kenneth Scott Kump, Waukesha, WI (US); Ping Xue, Pewaukee, WI (US); Donald Fayette Langler, Brookfield, WI (US); Brian John Kost, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 304 days.

(21) Appl. No.: 13/095,655

(22) Filed: Apr. 27, 2011

(65) Prior Publication Data

US 2012/0275678 A1 Nov. 1, 2012

(51) Int. Cl.
*G06K 9/00* (2006.01)

(52) U.S. Cl.
USPC .......... 382/132; 382/131; 378/62; 378/98.11; 378/98.12

(58) Field of Classification Search
CPC .......... G06T 2207/10072; G06T 2207/10116; G06T 2207/10081
USPC ............... 382/130, 131; 378/62, 98.11, 98.12
See application file for complete search history.

(56) References Cited

U.S. PATENT DOCUMENTS

| | | | |
|---|---|---|---|
| 5,452,338 A * | 9/1995 | Granfors et al. | 378/98.11 |
| 6,069,935 A | 5/2000 | Schick et al. | |
| 6,353,654 B1 * | 3/2002 | Granfors et al. | 378/62 |
| 6,366,622 B1 * | 4/2002 | Brown et al. | 375/322 |
| 6,380,528 B1 | 4/2002 | Pyyhtia et al. | |
| 6,475,146 B1 | 11/2002 | Frelburger et al. | |
| 6,801,598 B2 | 10/2004 | Tashiro et al. | |
| 7,006,600 B1 | 2/2006 | Krema et al. | |
| 7,038,588 B2 | 5/2006 | Boone et al. | |
| 7,116,807 B1 | 10/2006 | Brackett | |
| 7,343,565 B2 | 3/2008 | Ying et al. | |
| 7,502,445 B2 | 3/2009 | Shi et al. | |
| 7,549,961 B1 | 6/2009 | Hwang | |
| 7,755,059 B2 | 7/2010 | Liu et al. | |
| 7,873,145 B2 | 1/2011 | Liu et al. | |
| 2002/0050568 A1 | 5/2002 | Nonaka | |
| 2003/0081734 A1 | 5/2003 | Nicolas et al. | |
| 2004/0086077 A1 | 5/2004 | Moriyama | |

(Continued)

FOREIGN PATENT DOCUMENTS

| EP | 2293111 | * | 3/2011 |
|---|---|---|---|
| EP | 2293111 A1 | | 3/2011 |

(Continued)

OTHER PUBLICATIONS

U.S. Appl. No. 13/010,982, filed Jan. 21, 2011, Liu et al.

(Continued)

*Primary Examiner* — Stephen R Koziol
*Assistant Examiner* — Shaghayegh Azima
(74) *Attorney, Agent, or Firm* — Fletcher Yoder, P.C.

(57) ABSTRACT

A method for processing X-ray image data includes exposing a digital detector to X-ray radiation. The method also includes sampling data via the digital detector including X-ray image data and offset image data. The method further includes calculating an average offset image without prior knowledge of a total number of offset image frames sampled.

21 Claims, 9 Drawing Sheets

(56) References Cited

U.S. PATENT DOCUMENTS

| | | |
|---|---|---|
| 2005/0058239 A1* | 3/2005 | Mori ............................. 378/19 |
| 2005/0078793 A1* | 4/2005 | Ikeda ........................... 378/98.8 |
| 2005/0265267 A1 | 12/2005 | Hwang |
| 2006/0065846 A1 | 3/2006 | Ertel et al. |
| 2006/0222146 A1* | 10/2006 | Spahn ......................... 378/98.8 |
| 2006/0291624 A1* | 12/2006 | Xue et al. ...................... 378/98 |
| 2007/0116183 A1* | 5/2007 | Ueki et al. .................... 378/207 |
| 2007/0183567 A1 | 8/2007 | Rotondo et al. |
| 2007/0189462 A1 | 8/2007 | Spahn |
| 2007/0272873 A1 | 11/2007 | Jadrich et al. |
| 2008/0224056 A1 | 9/2008 | Liu et al. |
| 2008/0246065 A1* | 10/2008 | Takenaka et al. ............ 257/292 |
| 2009/0129546 A1 | 5/2009 | Newman et al. |
| 2009/0129653 A1* | 5/2009 | DeHority et al. ............. 382/132 |
| 2009/0207974 A1 | 8/2009 | Yi |
| 2009/0238330 A1* | 9/2009 | Luhta et al. .................... 378/19 |
| 2010/0020933 A1* | 1/2010 | Topfer et al. ............... 378/98.11 |
| 2010/0104066 A1 | 4/2010 | Foos et al. |
| 2010/0108898 A1 | 5/2010 | Liu et al. |
| 2010/0246757 A1 | 9/2010 | Liu et al. |
| 2011/0024644 A1 | 2/2011 | Yoshida et al. |
| 2011/0108710 A1* | 5/2011 | Yonekawa ................. 250/214 C |
| 2011/0121183 A1* | 5/2011 | Takenaka et al. .......... 250/361 R |
| 2011/0135052 A1* | 6/2011 | Proksa .............................. 378/5 |
| 2012/0312995 A1* | 12/2012 | Morf et al. ................ 250/363.01 |
| 2013/0032696 A1 | 2/2013 | Tajima |

FOREIGN PATENT DOCUMENTS

| | | |
|---|---|---|
| JP | 2001099944 A | 4/2001 |
| JP | 2006305228 A | 11/2006 |
| JP | 2010279403 | * 12/2010 |
| JP | 2010279403 A | 12/2010 |
| WO | 2011036901 A1 | 3/2011 |

OTHER PUBLICATIONS

U.S. Appl. No. 13/011,016, filed Jan. 21, 2011, Liu et al.
U.S. Appl. No. 13/011,033, filed Jan. 21, 2011, Liu et al.
PCT/US/2012/047390; International Search Report, mailed Nov. 7, 2012, 12 pages.
Search Report and Written Opinion from corresponding PCT Application No. PCT/US2012/034344 dated Jul. 5, 2012.
International Search Report and Written Opinion PCT/US12013/021091 Mailed on Jun. 7, 2013.

* cited by examiner

X-RAY SYSTEM AND METHOD FOR PROCESSING IMAGE DATA

BACKGROUND OF THE INVENTION

The subject matter disclosed herein relates to X-ray imaging systems and more particularly to X-ray imaging systems using digital detectors.

A number of radiological imaging systems of various designs are known and are presently in use. Such systems generally are based upon generation of X-rays that are directed toward a subject of interest. The X-rays traverse the subject and impact a film or a digital detector. Increasingly, such X-ray systems use digital circuitry for detecting the X-rays, which are attenuated, scattered or absorbed by the intervening structures of the subject. In medical diagnostic contexts, for example, such systems may be used to visualize internal tissues and diagnose patient ailments. In other contexts, parts, baggage, parcels, and other subjects may be imaged to assess their contents and for other purposes.

Basic X-ray systems may be designed for generating projection images only. Such projection images may be presented as a well-known reverse image, although the image data itself is subject to various presentations. In addition to projection X-ray systems, the art now offers fluoroscopy systems, computed tomography systems, and tomosynthesis systems that are based on similar X-ray radiation generation and detection. In computed tomography and tomosynthesis systems, for example, images are computed as slices through the subject based upon various reconstruction techniques applied to multiple collected images.

Various artifacts may be present in radiological system data collected in any one of the foregoing types of systems. Certain types of artifacts are well-known and can be handled, eliminated or corrected in various known ways. However, there are still artifacts that cannot be easily corrected or avoided, at least by known techniques. For example, X-ray systems with digital detectors suffer from artifacts due to the presence of electronic noise, particularly in applications where the X-ray dosage is low. In particular, an offset corrected image generated from image data and offset data may include even greater amounts of electronic noise compared to the original image. The problem is further exacerbated when the offset corrected image is generated from multiple imaging frames that include X-ray data increasing the electronic noise. Such electronic noise may adversely impact the quality of the image and, thus, the effective use of the image.

There is a need, therefore, for improved approaches to the elimination of electronic noise in radiological image data. There is a particular need for a technique that can address electronic noise in X-ray images.

BRIEF DESCRIPTION OF THE INVENTION

In accordance with one embodiment, a method for processing X-ray image data includes exposing a digital detector to X-ray radiation. The method also includes sampling data via the digital detector including X-ray image data and offset image data. The method further includes calculating an average offset image without prior knowledge of a total number of offset image frames sampled.

In accordance with another embodiment, a method for processing X-ray image data includes sampling data via a digital detector including X-ray image data and offset image data. The method also includes determining if sampled imaging frames include X-ray image data. The method further includes calculating an average offset image without prior knowledge of a total number of offset image frames sampled.

In accordance with a further embodiment, an X-ray imaging system includes an X-ray radiation source. The system also includes a digital detector configured to receive X-ray radiation from the source and to sample data including X-ray image data and offset image data. The system further includes processing circuitry configured to calculate an average offset image without prior knowledge of a total number of offset image frames sampled.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
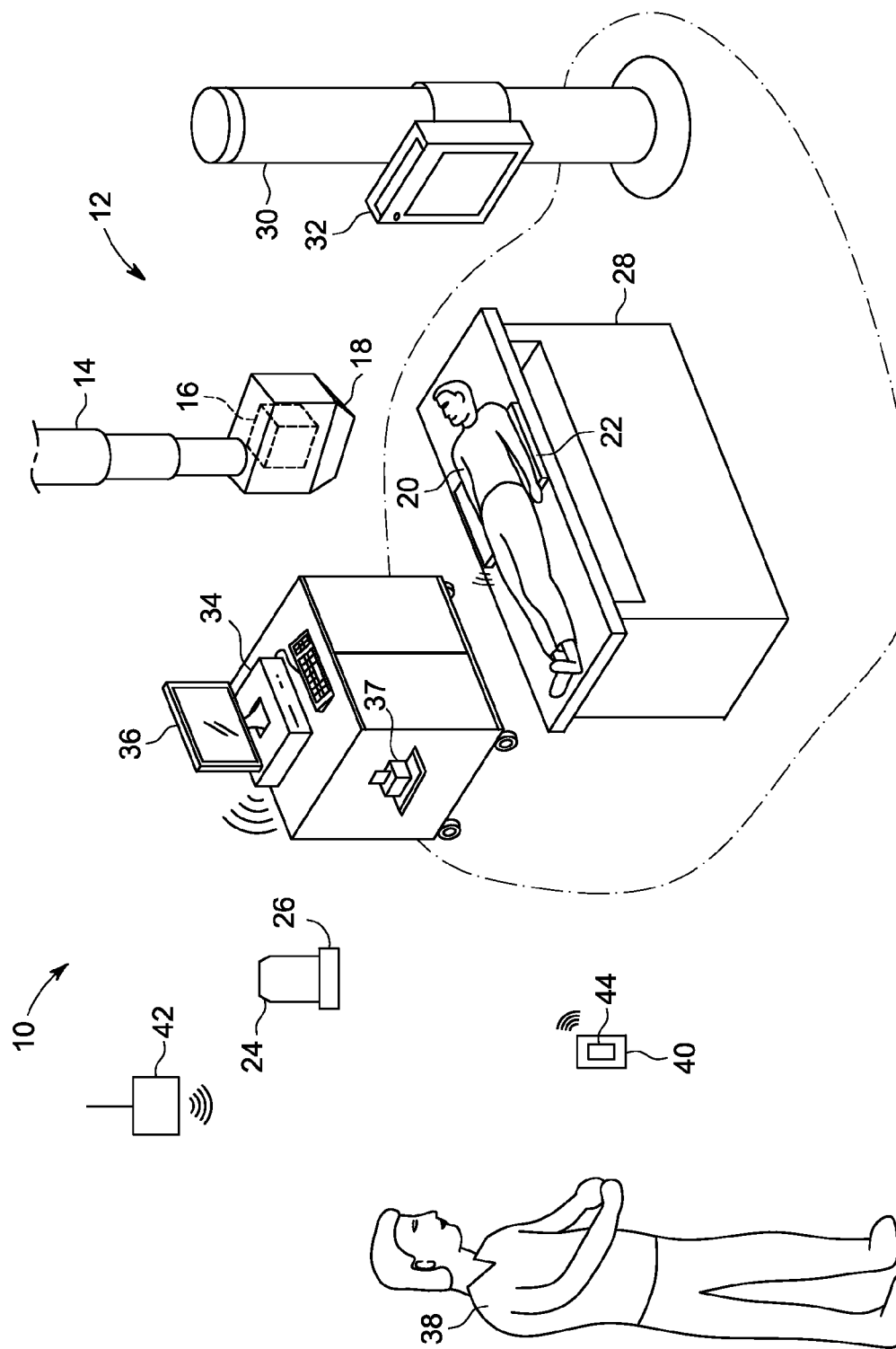
FIG. 1 is a perspective view of an exemplary X-ray system, equipped in accordance with aspects of the present technique.

Referring generally to FIG. 1, an X-ray system is represented, referenced generally by reference numeral 10. In the illustrated embodiment, the X-ray system 10, as adapted, is a digital X-ray system. In certain embodiments, the X-ray system may be a digital X-ray system without need of adaption. The X-ray system 10 is designed both to acquire image data and to process the image data for display in accordance with the present technique. Throughout the following discussion, however, while basic and background information is provided on the digital X-ray system used in medical diagnostic applications, it should be born in mind that aspects of the present techniques may be applied to digital detectors, including X-ray detectors, used in different settings (e.g., projection X-ray, computed tomography imaging, tomosynthesis imaging, fluoroscopy imaging, etc.) and for different purposes (e.g., parcel, baggage, vehicle and part inspection, etc.).

In the embodiment illustrated in FIG. 1, the X-ray system 10 includes an imaging system 12. The imaging system 12 may be a conventional analog imaging system, retrofitted for digital image data acquisition and processing as described below. Alternatively, the imaging system 12 may be a digital imaging system configured for digital image data acquisition and processing. In one embodiment, the imaging system 12 may be a stationary system disposed in a fixed X-ray imaging room, such as that generally depicted in and described below with respect to FIG. 1. It will be appreciated, however, that the presently disclosed techniques may also be employed with other imaging systems, including mobile X-ray units and systems in other embodiments. The imaging system 12 includes an overhead tube support arm 14 for positioning a radiation source 16, such as an X-ray tube, and a collimator 18 with respect to a patient 20 and a detector 22. The detector 22 includes a digital X-ray detector. In some embodiments, the detector 22 may be selected from a plurality of detectors 22, represented by detector 24, from a dock 26 (e.g., charging dock). Each detector 22 of the plurality of detectors 22 may be labeled and designed for a particular type of imaging (e.g., fluoroscopic and radiographic imaging). In certain embodiments, the detector 22 is configured to acquire X-ray image data without communication from a controller of the X-ray radiation source 16. In other words, the detector 22 is without communication of timing signals from the controller of the source 16 as to an X-ray exposure. As a result, in preparation for acquiring X-ray image data the detector 22 is configured to continuously sample data prior to and during an X-ray exposure. Also, the detector 22 is configured to combine multiple frames that include imaging data to generate X-ray images. In addition, the detector 22 is configured to at least partially process X-ray image data. In other embodiments, the detector 22 is configured to communicate with a controller of the X-ray radiation source 16 for receive communication of timing signals as to an X-ray exposure from the detector 22.

In one embodiment, the imaging system 12 may be used in consort with one or both of a patient table 28 and a wall stand 30 to facilitate image acquisition. Particularly, the table 28 and the wall stand 30 may be configured to receive detector 22. For instance, detector 22 may be placed on an upper, lower or intermediate surface of the table 28, and the patient 20 (more specifically, an anatomy of interest of the patient 20) may be positioned on the table 28 between the detector 22 and the radiation source 16. Also, the wall stand 30 may include a receiving structure 32 also adapted to receive the detector 22, and the patient 20 may be positioned adjacent the wall stand 30 to enable the image data to be acquired via the detector 22. The receiving structure 32 may be moved vertically along the wall stand 30.

Also depicted in FIG. 1, the imaging system 12 includes a workstation 34, display 36, and printer 37. In one embodiment, the workstation 34 may include or provide the functionality of the imaging system 12 such that a user 38, by interacting with the workstation 34 may control operation of the source 16 and detector 22. The detector 22 may be in communication with the workstation 34. The workstation 34 may house systems electronic circuitry that acquires image data from the detector 22 and that, where properly equipped (e.g., when the workstation 34 includes processing circuitry), may process the data to form desired images. In addition, the systems electronic circuitry both provides and controls power to the X-ray source 16. The workstation 34 may include buttons, switches, or the like to facilitate operation of the X-ray source 16 and detector 22. In other embodiments, the functions of the imaging system 12 may be decentralized, such that some functions of the imaging system 12 are performed at the workstation 34 (e.g., controlling operation of the source 16, while other functions (e.g., controlling operation of the detector 22) are performed by another component of the X-ray system 10, such as a portable detector control device 40. The portable detector control device 40 may include a personal digital assistant (PDA), palmtop computer, laptop computer, smart telephone, tablet computer such as an iPad™, or any suitable general purpose or dedicated portable interface device. The portable detector control device 40 is configured to be held by the user 38 and to communicate wirelessly with the detector 22. It is noted that the detector 22 and portable detector control device 40 may utilize any suitable wireless communication protocol, such as an IEEE 802.15.4 protocol, an ultra wideband (UWB) communication standard, a Bluetooth communication standard, or any IEEE 802.11 communication standard. Alternatively, the portable detector control device may be configured to be tethered or detachably tethered to the detector 22 to communicate via a wired connection.

In certain embodiments, the portable detector control device 40 is also configured to communicate instructions (e.g., detector operating mode) to the detector 22 for the acquisition of X-ray image data. In turn, the detector 22 may be configured to prepare for an X-ray exposure in response to instructions from the portable detector control device 40, and to transmit a detector ready signal to the device 40 indicating that the detector 22 is prepared to receive the X-ray exposure. The device 40 may also be configured to communicate patient information or X-ray technique information to the detector 22. Similar to the detector 22, the device 40 may be without communication from the controller of the X-ray source 16. Further, the portable detector control device 40 is configured to receive X-ray image data from the detector 22 for processing and image reconstruction. Indeed, both the detector 22 and the portable detector control device 40 are configured to at least partially process the X-ray image data. However, in certain embodiments, the detector 22 and/or the portable detector control device 40 are configured to fully process the X-ray image data. Alternatively, the workstation 34 may process the X-ray image data. Also, the workstation 34, the detector 22, and/or the device 40 is configured to generate a DICOM compliant data file based upon the X-ray image data, patient information, and other information. Further, the workstation 34, the detector 22 and/or the device 40 is configured to wirelessly transmit (or via a wired connection) processed X-ray image data (e.g., partially or fully processed X-ray image data) to an institution image review and storage system over a network 42. The institution image review and storage system may include a hospital information system (HIS), a radiology information system (RIS), and/or picture archiving communication system (PACS). In some embodiments, the institution image review and storage system may process the X-ray image data. In one embodiment, the workstation 34 may be configured to function as a server of instructions and/or content on a network 42 of the medical facility. The workstation 34, detector 22, and/or device 40 are also configured to transmit, via a wired or wireless connection, processed X-ray images to the printer 37 to generate a copy of the image.

The portable detector control device 40 includes a user-viewable screen 44 and is configured to display patient data and reconstructed X-ray images based upon X-ray image data on the screen 44. The screen 44 may include a touch-screen and/or input device (e.g., keyboard) configured to input data (e.g., patient data) and/or commands (e.g., to the detector). For example, the device 40 may be used to input patient information and other imaging related information (e.g., type of source 16, imaging parameters, etc.) to form a DICOM image header. In one embodiment, the patient information may be transferred from a patient database via a wireless or wired connection from the network or the workstation 34 to the device 40. The detector 22 and/or device may incorporate the information for the image header with the X-ray image to generate the DICOM compliant data file. Also, the device 40 may be used to navigate X-ray images displayed on the screen 44. Further, the device 40 may be used to modify the X-ray images, for example, by adding position markers (e.g., "L"/ "R" for left and right, respectively) onto the image. In one embodiment, metal markers may be placed on the detector 22 to generate position markers.

In one embodiment, the imaging system 12 may be a stationary system disposed in a fixed X-ray imaging room, such as that generally depicted in and described above with respect to FIG. 1. It will be appreciated, however, that the presently disclosed techniques may also be employed with other imaging systems, including mobile X-ray units and systems, in other embodiments.

The X-ray system 10 is not intended to be limited to any specific type of imaging system or modality. For example, the X-ray system 10 may employ digital X-ray tomosynthesis. Digital X-ray tomosynthesis is an imaging technique that enables three-dimensional imaging of the patient 20 using a large-area digital detector 22 typically used for conventional (single projection) radiography. In clinical tomosynthesis techniques, the source of X-ray radiation 16 is moved between imaging positions and multiple images are made by casting an X-ray beam on the digital detector 22. In certain applications, multiple, distributed and static X-ray sources may be used, or movable sources may be displaced in various patterns or trajectories. In certain systems, the detector 22 is also moved during this process. Three-dimensional data is reconstructed in the form of a number of slices through the patient anatomy, each parallel to the detector plane. Tomosynthesis acquisition consists of a number of projections (X-ray exposures) covering an angular range of less than 180°, and typically between 20° and 40°.

Figure 2:
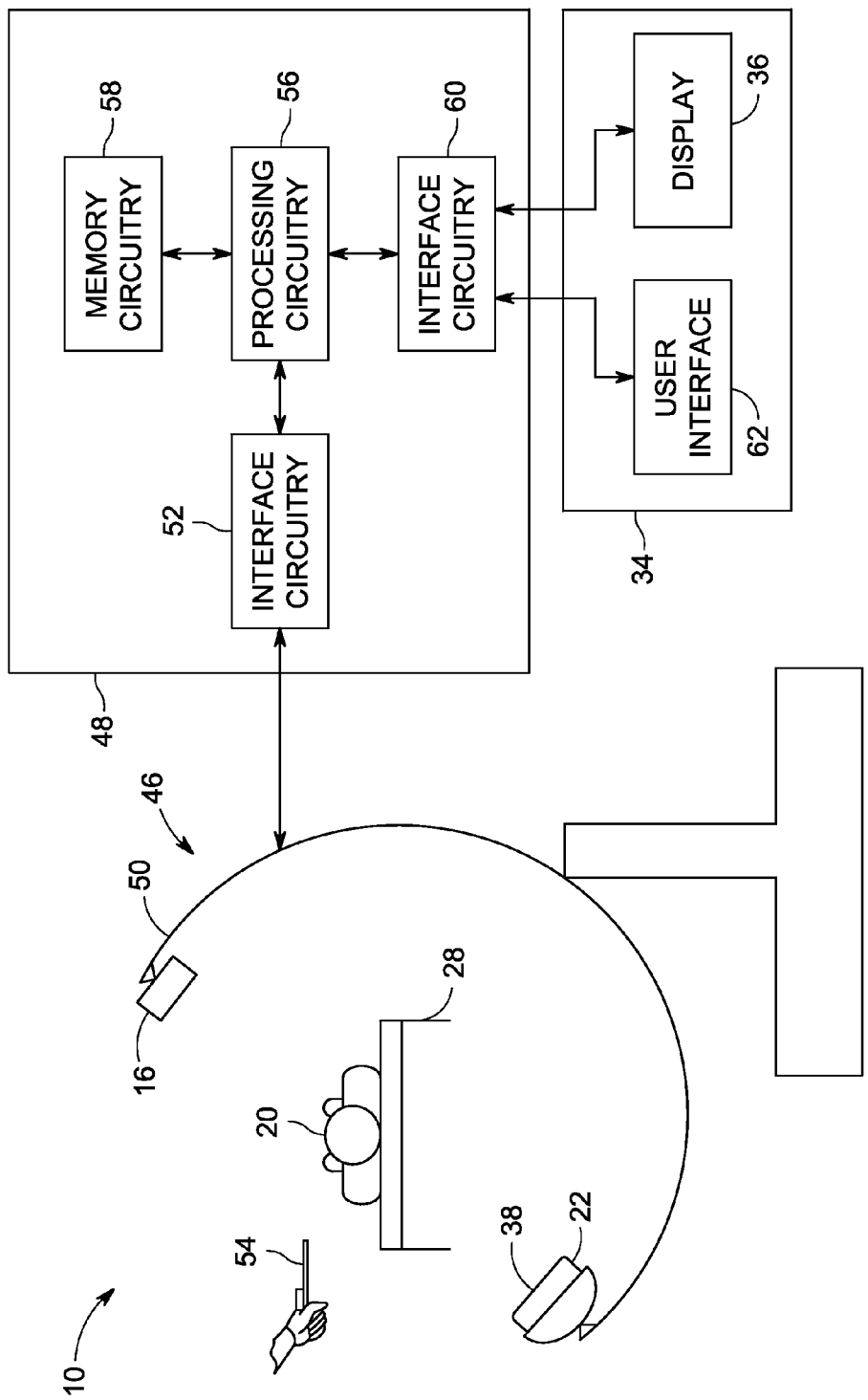
FIG. 2 is a schematic view of an exemplary X-ray system including a fluoroscopy imaging system, equipped in accordance with aspects of the present technique.

Referring now to FIG. 2, another example of an X-ray system 10 is illustrated. The X-ray system 10 includes an X-ray fluoroscopy system 46 for acquiring and processing image data. As illustrated, the X-ray system 10 includes controller 48 and workstation 34. X-ray fluoroscopy system 46 is illustrated as a C-arm system that includes a C-arm 50, X-ray radiation source 16, and X-ray detector 22. The X-ray radiation source 16 is mounted on the C-arm 50, and the X-ray detector 22 is mounted on the C-arm 50 in an opposing location from the X-ray radiation source 28. While in some systems the X-ray radiation source 16 and the X-ray detector 22 may be fixed, in a typical fluoroscopy system the C-arm 50 allows for movement of the X-ray radiation source 16 and the X-ray detector 22 about the patient 20. In operation, the X-ray radiation source 16 emits a stream of radiation suitable for X-ray fluoroscopy. The X-ray detector 22 receives a portion the stream of radiation from the X-ray source 16 that passes through patient 20 positioned on a table 28. The X-ray detector 22 produces electrical signals that represent the intensity of the radiation stream. As those of ordinary skill in the art will appreciate, these signals are suitably acquired and processed to reconstruct an image of features within the subject.

As previously mentioned, the X-ray system 10 further includes controller 22. In the illustrated embodiment, controller 48 includes interface circuitry 52 for receiving imaging and tracking data (e.g., to track a medical device 54 such as a surgical device or any other suitable deice for use in a medical procedure), processing circuitry 56, memory circuitry 58, and workstation interface circuitry 60 for communicating with workstation 34. As will be appreciated, one or more computers may be used to implement controller 48. In general, processing circuitry 56, which may typically include a digital signal processor, a CPU or the like, may process the tracking data so that the location of the device 54 may be projected onto the reconstructed image. In addition, processing circuitry 42 also may process the imaging data (e.g., image data and offset data) to reconstruct the data into a meaningful diagnostic image. Memory circuitry 58 may serve to save the imaging and tracking data as well as other system parameters.

As illustrated, the X-ray system 10 further includes the workstation 34, which includes a user interface 62 and display 36. The user interface 62 may include a keyboard and/or mouse, as well as other devices such as printers or other peripherals for reproducing hardcopies of the reconstructed images. Display 36 may include one or more screens. For example, the display 36 may include a first screen for displaying a previously acquired image and a second screen for displaying one or more intra-operative images.

Figure 3:
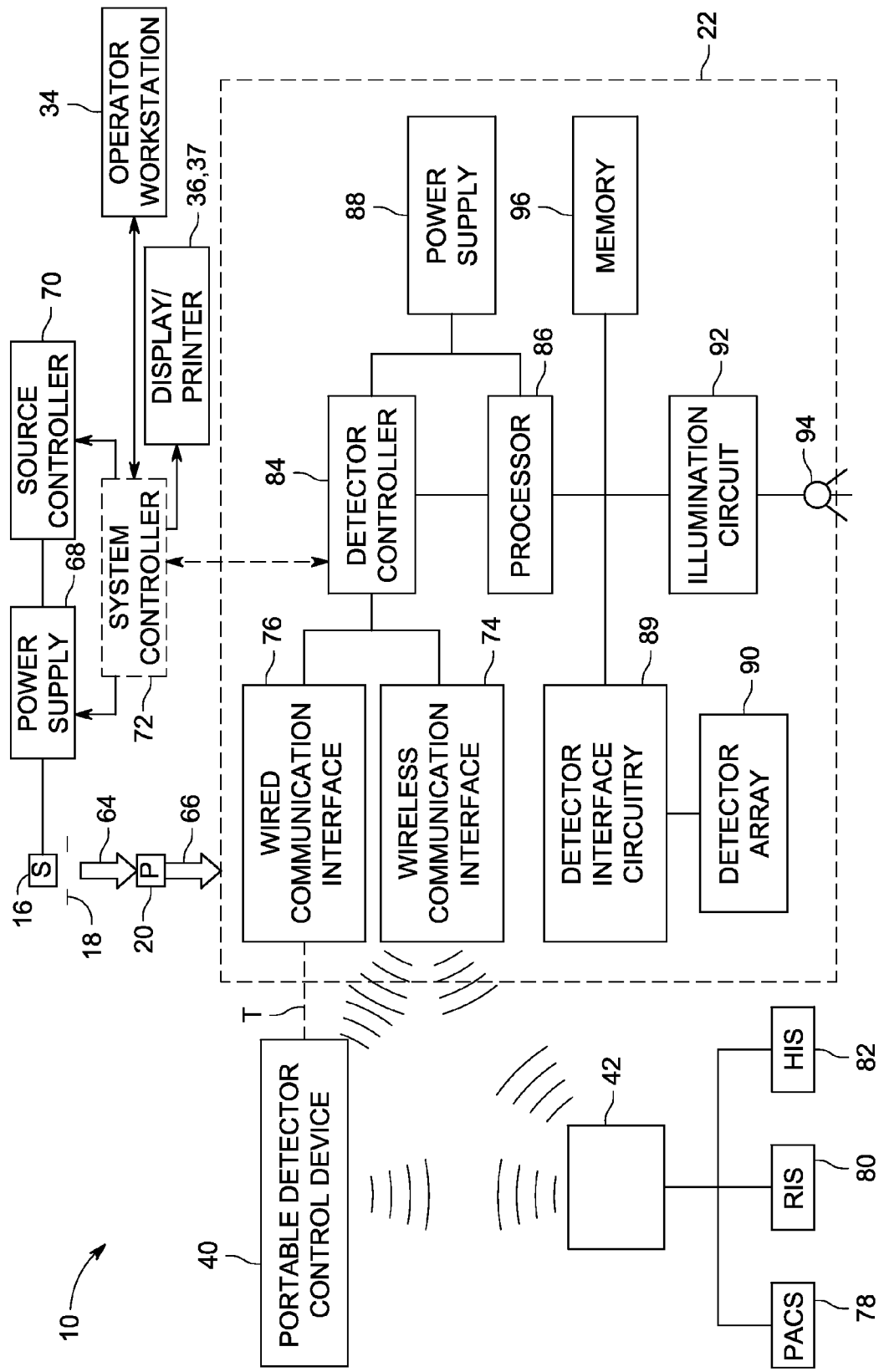
FIG. 3 is a diagrammatical overview of the X-ray system in FIGS. 1 and 2.

FIG. 3 is a diagrammatical overview of the X-ray system 10 in FIGS. 1 and 2 illustrating the components of the system 10 in more detail. The imaging system 10 includes the X-ray radiation source 16 positioned adjacent to a collimator 18. Collimator 18 permits a stream of radiation 64 to pass into a region in which a subject 20, such as a human patient 20, is positioned. A portion of the radiation 66 passes through or around the subject 20 and impacts the digital X-ray detector 22. As described more fully below, detector 22 converts the X-ray photons received on its surface to lower energy photons, and subsequently to electric signals which are acquired and processed to reconstruct an image of the features within the subject 20.

The source 16 is coupled to a power supply 68 which furnishes power for examination sequences. The source 16 and power supply 52 are coupled to a source controller 70 configured to command X-ray emission of X-rays for image exposures. As mentioned above, in certain embodiments, the detector 22 is configured to acquire X-ray image data (e.g., image data and offset data) without communication from the source controller 70. Instead, the detector 22 is responsive to the portable detector control device 40 configured to communicate instructions to the detector 22 for acquisition of the X-ray image data. In addition, the portable detector control device 40 is configured to receive the X-ray image data from the detector 22 for processing and imaging reconstruction.

In other embodiments, both the power supply 68 and source controller 70 are responsive to signals from a system controller 72. In general, system controller 72 commands operation of the imaging system to execute examination protocols and to process acquired image data. In the present context, system controller 72 also includes signal processing circuitry, typically based upon a general purpose or application-specific digital computer, associated memory circuitry for storing programs and routines executed by the computer, as well as configuration parameters and image data, interface circuits, and so forth. The system controller 72 is linked to at least one output device, such as display 36 or printer 37. The output device may include standard or special purpose computer monitors and associated processing circuitry. One or more operator workstations 34 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The detector 22 includes a wireless communication interface 74 for wireless communication with the device 40, as well as a wired communication interface 76, for communicating with the device 40 when it is tethered to the detector 22. The detector 22 and the device may also be in communication with the institution image review and storage system over the network 42 via a wired or wireless connection. As mentioned above, the institution image review and storage system may include PACS 78, RIS 80, and HIS 82. It is noted that the wireless communication interface 74 may utilize any suitable wireless communication protocol, such as an ultra wideband (UWB) communication standard, a Bluetooth communication standard, or any 802.11 communication standard. Moreover, detector 22 is coupled to a detector controller 84 which coordinates the control of the various detector functions. For example, detector controller 84 may execute various signal processing and filtration functions, such as for initial adjustment of dynamic ranges, interleaving of digital image data, and so forth. In certain embodiments, the detector controller 84 is responsive to signals from the device 40. In other embodiments, the detector controller 84 is response to signals from the system controller 72. The detector controller 84 is linked to a processor 86. The processor 86, the detector controller 84, and all of the circuitry receive power from a power supply 88. The power supply 88 may include one or more batteries.

Also, the processor 86 is linked to detector interface circuitry 89. The detector 22 converts X-ray photons received on its surface to lower energy photons. The detector 22 includes a detector array 90 that includes an array of photodetectors to convert the light photons to electrical signals. Alternatively, the detector 22 may convert the X-ray photons directly to electrical signals. These electrical signals are converted to digital values by the detector interface circuitry 89 which provides the values to the processor 86 to be converted to imaging data and sent to the device 40 and/or system controller 72 to reconstruct an image of the features within the subject 20. In one embodiment, the detector 22 may at least partially process or fully process the imaging data (e.g., image data and offset data). Alternatively, the imaging data may be sent from the detector 22 to a server to process the imaging data.

The processor 86 is also linked to an illumination circuit 92. The detector controller 84, in response to a signal received from the device 40, may send a signal to the processor 86 to signal the illumination circuit 92 to illuminate a light 94 to indicate the detector 22 is prepared to receive an X-ray exposure in response to the signal. Indeed, in response to a signal from the device 40, the detector 22 may be turned on or awoken from an idle state. Alternatively, the detector 22 may be turned on directly or awoken from an idle state by the user (e.g., pressing an on/off button located on the detector 22).

Further, the processor is linked to a memory 96. The memory 96 may store various configuration parameters, calibration files, and detector identification data. In addition, the memory 96 may store patient information received from the device 40 to be combined with the image data to generate a DICOM compliant data file. Further, the memory 96 may store sampled data (e.g., image data and offset data) gathered during the imaging mode as well as X-ray images. As mentioned above, in some embodiments, the device 40 may conduct the image processing and incorporate a DICOM header to generate a DICOM compliant data file.

Figure 4:
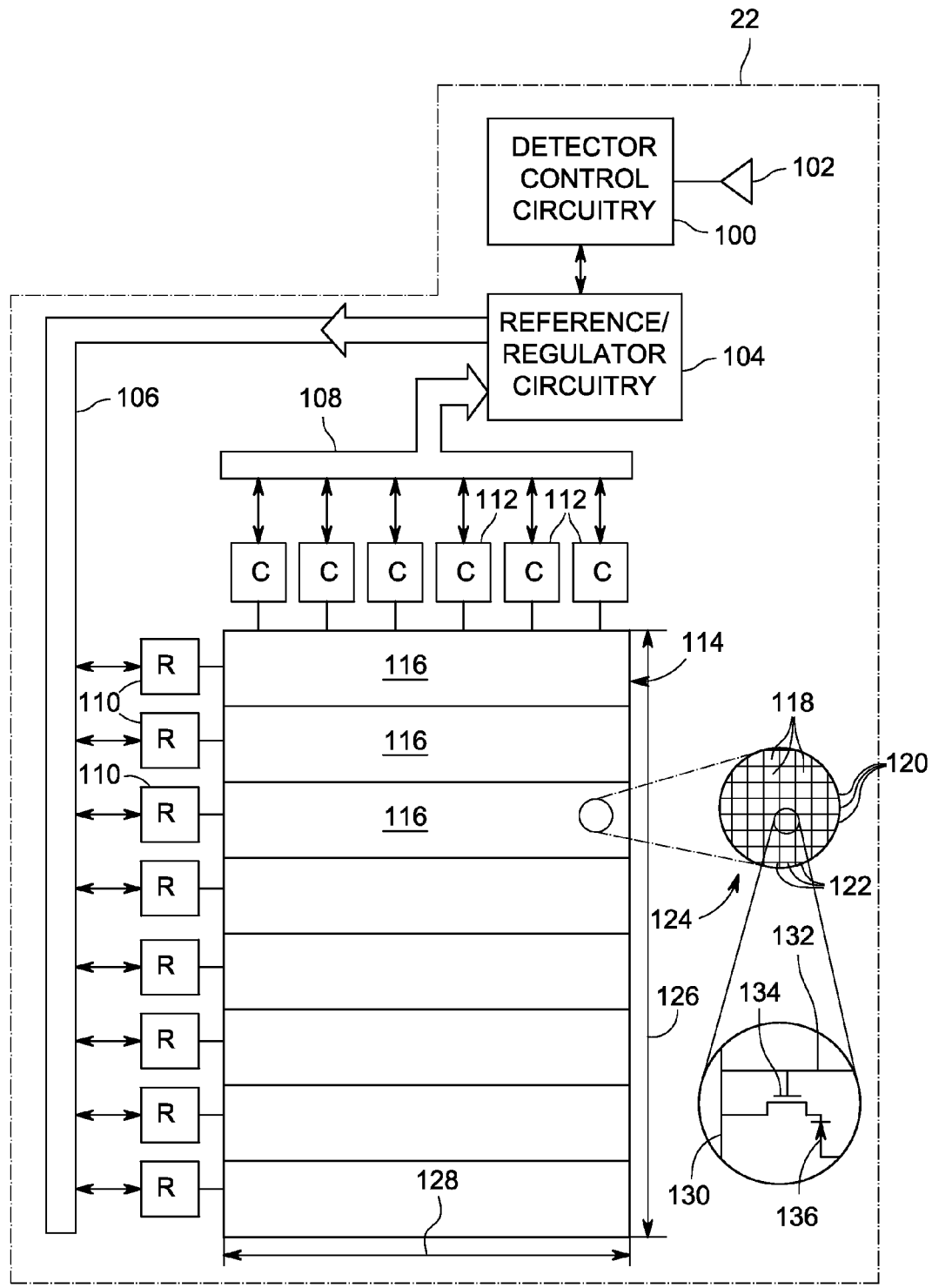
FIG. 4 is a diagrammatical representation of functional components in a detector of the system of FIGS. 1-3.

FIG. 4 is a diagrammatical representation of functional components of digital detector 22. As illustrated, detector control circuitry 102 receives DC power from a power source, represented generally at reference numeral 104. Detector control circuitry 100 is configured to originate timing and control commands for row and column electronics used to acquire image data during data acquisition phases of operation of the system. Circuitry 100 therefore transmits power and control signals to reference/regulator circuitry 104, and receives digital image pixel data from circuitry 104.

In a present embodiment, detector 22 consists of a scintillator that converts X-ray photons received on the detector surface during examinations to lower energy (light) photons. An array of photodetectors then converts the light photons to electrical signals which are representative of the number of photons or the intensity of radiation impacting individual pixel regions or picture elements of the detector surface. In certain presently contemplated, the X-ray photons may be directly converted to electrical signals. Readout electronics convert the resulting analog signals to digital values that can be processed, stored, and displayed, such as on device 40 following reconstruction of the image. In a present form, the array of photodetectors is formed of amorphous silicon. The array of photodetectors or discrete picture elements is organized in rows and columns, with each discrete picture element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual channel of the readout electronics.

As described in greater detail below, the detector control circuitry 100 is configured to sample data (e.g., image data and offset data) from the discrete picture elements prior to and during receipt of X-ray radiation. Sampled data (e.g., offset data) collected prior to receipt of the X-ray radiation may be stored by the detector control circuitry 100 for use in calculating an average offset image, generating one or more offset corrected images, and reconstructing a user-viewable image from the X-ray image data. Further, the detector control circuitry 100 is configured to sample data, including X-ray image data, from the discrete picture elements during receipt of X-ray radiation.

Turning back to the embodiment illustrated in FIG. 4, by way of example, a row bus 106 includes a plurality of conductors for enabling readout from various rows of the detector 22, as well as for disabling rows and applying a charge compensation voltage to selected rows, where desired. A column bus 108 includes additional conductors for reading out signals from the columns while the rows are sequentially enabled. Row bus 106 is coupled to a series of row drivers 110, each of which commands enabling of a series of rows in the detector 22. Similarly, readout electronics 112 are coupled to column bus 108 for reading out signals from all columns of the detector 22.

In the illustrated embodiment, row drivers 110 and readout electronics 112 are coupled to a detector panel 114 which may be subdivided into a plurality of sections 116. Each section 116 is coupled to one of the row drivers 110, and includes a number of rows. Similarly, each column module 112 is coupled to a series of columns. The photodiode and thin film transistor arrangement mentioned above thereby define a series of pixels or discrete picture elements 118 which are arranged in rows 120 and columns 122. The rows and columns define an image matrix 124, having a height 126 and a width 128.

As also illustrated in FIG. 4, each picture element 118 is generally defined at a row and column crossing, at which a column electrode 130 crosses a row electrode 132. As mentioned above, a thin film transistor 134 is provided at each crossing location for each picture element, as is a photodiode 136. As each row is enabled by row drivers 110, signals from each photodiode 136 may be accessed via readout electronics 112, and converted to digital signals for subsequent processing and image reconstruction. Thus, an entire row of picture elements 118 in the array is controlled simultaneously when the scan line attached to the gates of all the transistors 134 of picture elements 118 on that row is activated. Consequently, each of the picture elements 118 in that particular row is connected to a data line, through a switch, which is used by the readout electronics to restore the charge to the photodiode 136.

It should be noted that in certain systems, as the charge is restored to all the picture elements 118 in a row simultaneously by each of the associated dedicated readout channels, the readout electronics is converting the measurements from the previous row from an analog voltage to a digital value. Furthermore, the readout electronics may transfer the digital values from rows previous to the acquisition subsystem, which will perform some processing prior to displaying a diagnostic image on a monitor or writing it to film.

The circuitry used to enable the rows may be referred to in a present context as row enable or field effect transistor (FET) circuitry based upon the use of field effect transistors for such enablement (row driving). The FETs associated with the row enable circuitry described above are placed in an "on" or conducting state for enabling the rows, and are turned "off" or placed in a non-conducting state when the rows are not enabled for readout. Despite such language, it should be noted that the particular circuit components used for the row drivers and column readout electronics may vary, and the present invention is not limited to the use of FETs or any particular circuit components.

In accordance with the present techniques, the data (e.g., image data and offset) acquired or sampled by system 10 may be perturbed by various sources of electronic noise depending upon the context in which the system is used. In particular, offset images collected during the sampling of the data may increase the electronic noise in an offset corrected image compared to the original image. The system 10 allows for the reduction of the electronic noise in the offset corrected image, thus, reducing artifacts that would otherwise be present in the image data and visible in reconstructed images based upon the data. In particular, the system 10 takes the total offset image frames sampled or acquired and calculates an average offset correction image, which is used in combination with one or more sampled imaging frames that include X-ray image data, to generate an offset corrected image frame with reduced electronic noise. The calculation of the average offset image occurs without prior knowledge of the total number of offset image frames. In particular, the average offset image frame may be calculated as each offset image frame is sampled. Alternatively, the average offset image frame may be calculated subsequent to sampling the total number of offset image frames (e.g., post-processing). The reduction in electronic noise may be carried out in any of the foregoing circuitry, including the detector circuitry, the detector controller, or the system controller. Moreover, where desired, the electronic noise reduction may occur remote from the detector and imaging system, e.g., in the portable detector control device 40 or institution image review and storage system over the network 42. The institution image review and storage system that may include HIS, RIS, and/or PACS.

Figure 5:
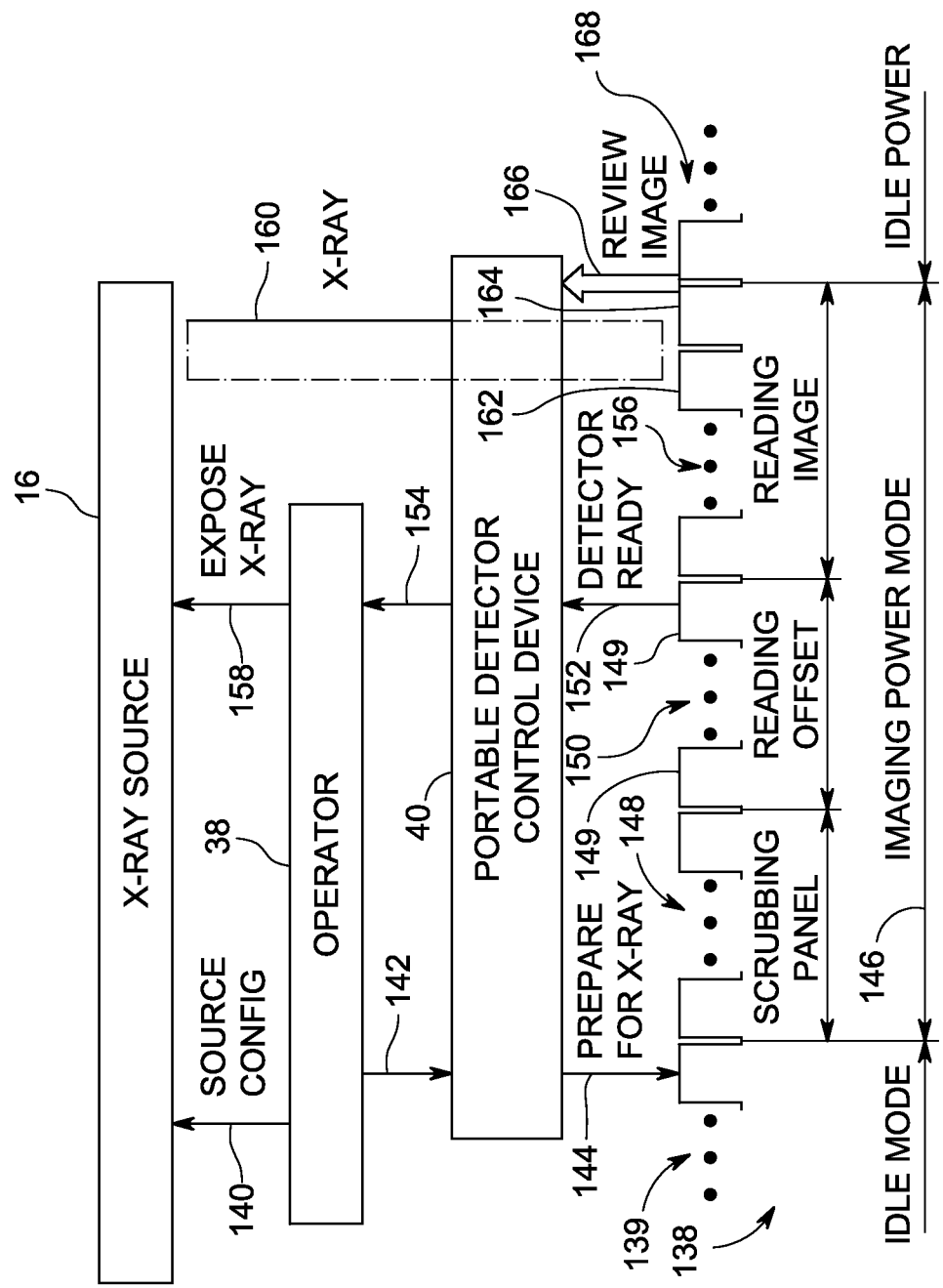
FIG. 5 is a diagrammatical representation of an acquisition sequence for an imaging application in which a detector is without a priori knowledge of the beginning and ending times of an exposure, and both image data and offset data are acquired, in accordance with aspects of the present technique.
Figure 6:
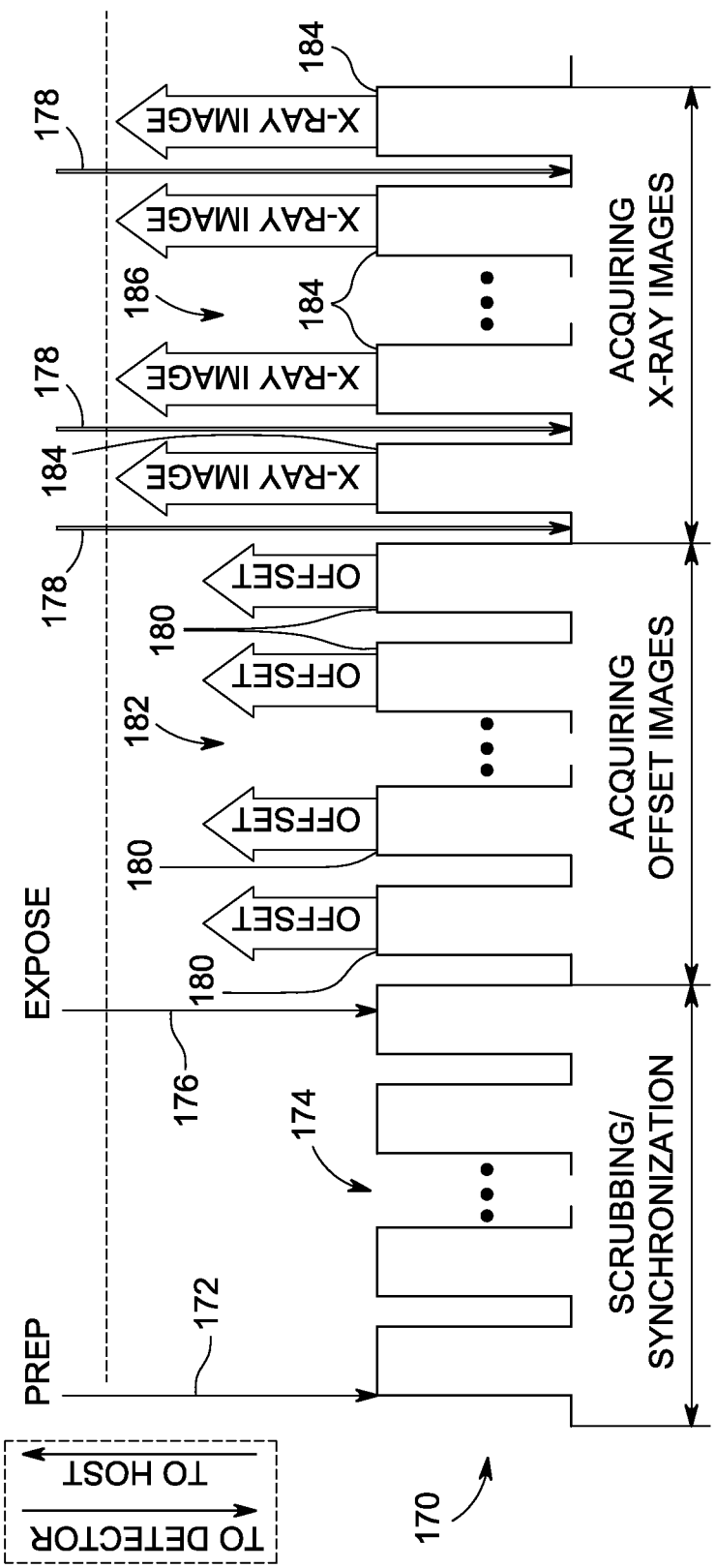
FIG. 6 is diagrammatical representation of an acquisition sequence for a tomosynthesis imaging application in which both image data and offset data are acquired, in accordance with aspects of the present technique.
Figure 7:
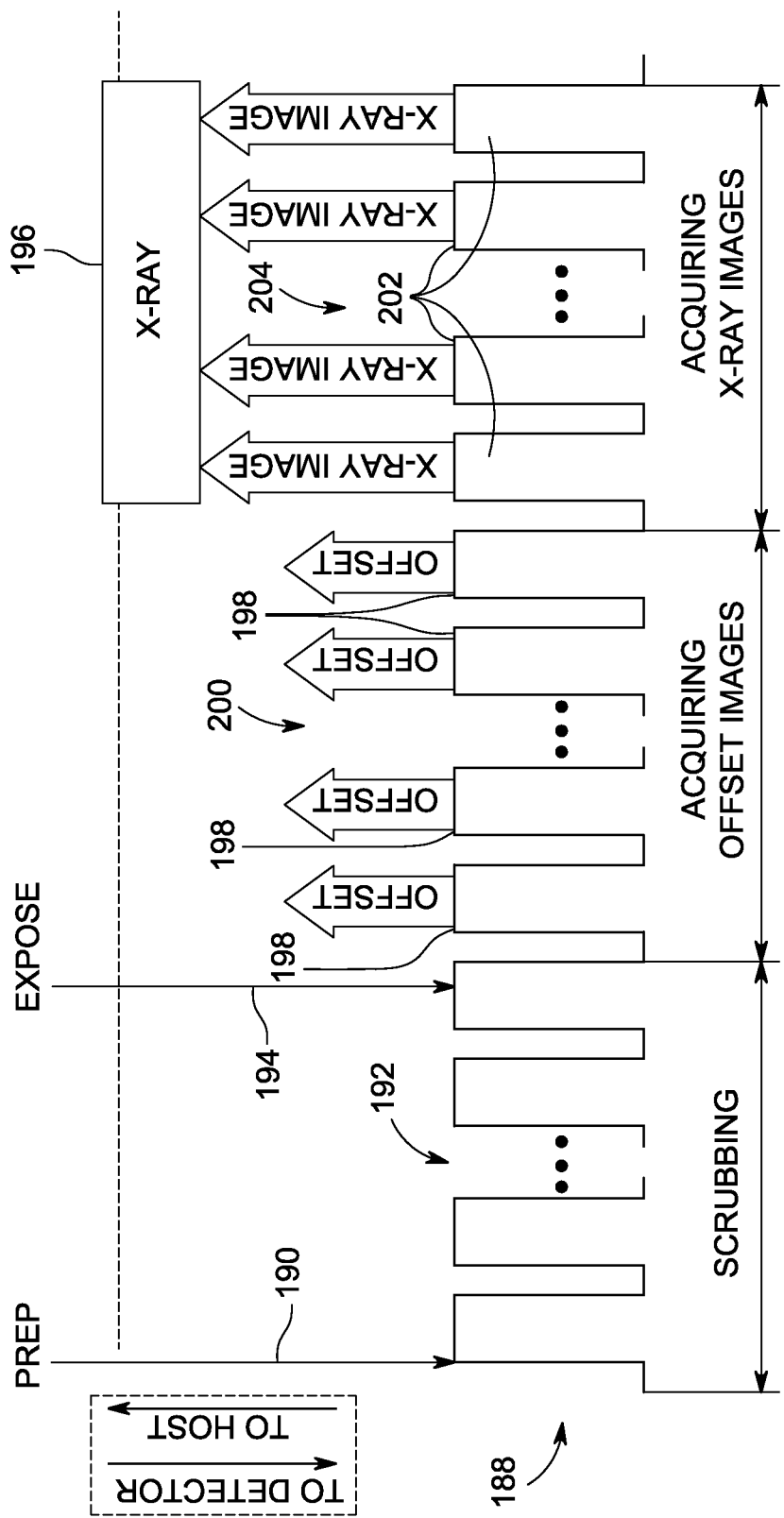
FIG. 7 is a diagrammatical representation of an acquisition sequence for a fluoroscopy imaging application in which both image data and offset data are acquired, in accordance with aspects of the present technique.

Many of the imaging applications mentioned above produce numerous offset image frames that would useful in calculating the average offset image to reduce electronic noise in generating one or more offset corrected images. FIGS. 5-7 illustrate examples of acquisition sequences for some of these imaging applications. For example, in certain embodiments, the detector 22 is without communication from the source controller 70 and, thus, is without a priori knowledge of the beginning and ending times of an exposure. In one embodiment, the detector 22 is configured to detect the beginning and ending of the X-ray exposure automatically and to form an X-ray image without communication with the detector control device 40. In another embodiment, the detector 22 is configured to stay in idle power mode and switch to imaging power mode after receiving a command from the detector control device 40. The detector 22 starts detecting the beginning and ending of the X-ray exposure after it is switched into full power mode. This results in a unique workflow dynamic between the imaging system 12, detector 22, and portable detector controller device 40 as illustrated in FIG. 5.

FIG. 5 is a diagrammatical representation of an acquisition sequence for an imaging application in which the detector 22 is without a priori knowledge of the beginning and ending times of an exposure, and both image data and offset data are acquired for generating one or more offset corrected images and producing user-viewable images. FIG. 5 includes an acquisition sequence 138 of the detector 22 corresponding to the interaction between the detector 22, portable detector control device 40, the operator or user 38, and the X-ray source 16. The detector 22, device 40, and operation of the source 16 are as described above. While the detector 22 is in idle mode, represented by region 139 of the sequence 138, the operator 38 configures the source 16 as indicated by arrow 140. Configuring the source 16 may include setting exposure parameters and the type of exposure. Also, while the detector 22 remains in idle mode, the operator 38 may position the imaging subject and the source 16. Further, the operator 38 enters instructions into device 40, as indicated by arrow 142, and sends instructions 144 to the detector 22 to prepare for exposure.

Upon receiving the instructions to prepare for acquisition of X-ray image data, the detector 22 enters imaging power mode 146. The detector 22 begins by scrubbing the panel, as indicated by region 148 of the acquisition sequence 138, to equilibrate the circuitry on the panel. Then, the detector 22 reads multiple offset image frames 149 from the panel (e.g., region 150), upon which the detector 22 sends a detector ready signal 152 to the device 40. In one embodiment, the device 40 provides a visual indication (e.g., flashing LED) to indicate the ready state of the detector 22. In another embodiment, the device 40 provides an audio indication. In a further embodiment, the device 40 provides both visual and audio indications. The operator 38 receives the ready signal on the device 40, as indicated by arrow 154. Once the detector 22 is ready, the detector 22 begins continuously sampling or reading frames as indicated by region 156 of the acquisition sequence 138 to detect an exposure. At any time, the operator may initiate the exposure, as indicated by arrow 158, from the source 16. Upon initiation of the exposure, the detector 22 receives the X-ray radiation 160 from the source 16. The detector 22 samples the frames to determine the beginning and ending frames that span the exposure (e.g., frames 162 and 164). After termination of the exposure, the detector 22 may process the acquired data (e.g., image and offset data) and send a preview of a reconstructed image, indicated by arrow 166, to the device 40 for viewing by the operator 38. Processing the offset data enables the calculation of an average offset image, which may be used along with the image data to subsequently generate an offset corrected image. The average offset image may be calculated without prior knowledge of the total number of offset image frames 149 sampled. The offset image frames 49 may include frames acquired in both regions 150 and 156. In certain embodiments, the average offset image may be calculated as each offset image frame 149 is acquired by the detector 22. Alternatively, the data (e.g., image and offset data) may be sent to the device 40 for further processing and the generation of the reconstructed image. After the exposure ends, the detector 22 reverts back to idle mode as indicated by region 168 of the acquisition sequence 138.

As mentioned above, the detector 22 shifts from an idle mode to an imaging power mode. In the imaging power mode, the panel in the detector 22 is continuously read, since the detector 22 lacks a priori knowledge (or data) of when the exposure may occur. Thus, reading or sampling of data from the panel occurs prior to and during the exposure acquiring numerous offset image frames 149 and one or more imaging frames (e.g., 162 and 164) that include X-ray image data. Normally, combining one or more imaging frames that include X-ray image data significantly increases the amount of electronic noise in the generated offset corrected image. However, as described in greater detail below, the techniques to average the total number of sampled offset image frames 149 significantly reduces the electronic noise.

FIG. 6 is diagrammatical representation of an acquisition sequence for a tomosynthesis imaging application in which both image data and offset data are acquired for generating one or more offset corrected images and producing user-viewable images. FIG. 6 includes an acquisition sequence 170 of the detector 22 corresponding to the interaction between the detector 22, a host (e.g., system controller of the imaging system), and the X-ray source 16. The detector 22 and operation of the source 16 are as described above.

Upon receiving a signal 172 to prepare for acquisition of X-ray image data, the detector 22 begins scrubbing the panel as indicated by region 174 of the acquisition sequence 170. Scrubbing of the panel equilibrates the circuitry on the panel. Following scrubbing, the detector 22 receives a signal 176 indicating the start of the exposure. In response to the signal 176 and prior to receiving multiple pulses of X-ray radiation 178, the detector 22 begins sampling or acquiring multiple offset images frames 180 as indicated by region 182 of the acquisition sequence 170. Upon the detector 22 receiving the pulses of X-ray radiation 178, the detector 22 samples one or more imaging frames 184 that include X-ray image data for each pulse of X-ray radiation 178 as indicated by region 186 of the acquisition sequence 170. After termination of the exposure, the detector 22 may process the acquired data (e.g., image and offset data). In contrast to the imaging application in FIG. 5, the X-ray system 10 using the tomosynthesis imaging application possesses information to determine when the X-ray source 16 exposes X-ray radiation onto the detector 22 and when the imaging frames are changed from offset image frames 182 to imaging frames that include X-ray image data. As mentioned above, processing the offset data enables the calculation of an average offset image, which may be used along with the image data to subsequently generate an offset corrected image. The average offset image may be calculated without prior knowledge of the total number of offset image frames 182 sampled. As described in greater detail below, the techniques to average the total number of sampled offset image frames 182 significantly reduces the electronic noise. In certain embodiments, the average offset image may be calculated as each offset image frame 182 is acquired by the detector 22. Alternatively, the data (e.g., image and offset data) may be sent to the system controller or institution image review and storage system that may include HIS, RIS, and/or PACS for processing. As described in greater detail below, the techniques to average the total number of sampled offset image frames significantly reduces the electronic noise.

FIG. 7 is diagrammatical representation of an acquisition sequence for a fluoroscopy imaging application in which both image data and offset data are acquired for generating one or more offset corrected images and producing user-viewable images. FIG. 7 includes an acquisition sequence 188 of the detector 22 corresponding to the interaction between the detector 22, a host (e.g., system controller of the imaging system), and the X-ray source 16. The detector 22 and operation of the source 16 are as described above.

Upon receiving a signal 190 to prepare for acquisition of X-ray image data, the detector 22 begins scrubbing the panel as indicated by region 192 of the acquisition sequence 188. Scrubbing of the panel equilibrates the circuitry on the panel. Following scrubbing, the detector 22 receives a signal 194 indicating the start of the exposure. In response to the signal 194 and prior to receiving the X-ray radiation 196, the detector 22 begins sampling or acquiring multiple offset images frames 198 as indicated by region 200 of the acquisition sequence 188. In contrast to the tomosynthesis imaging application described above in FIG. 6, the exposure to X-ray radiation 196 is continuous. Upon the detector 22 receiving the X-ray radiation 196, the detector 22 samples one or more imaging frames 202 that include X-ray image data during the exposure to the X-ray radiation 196 as indicated by region 204 of the acquisition sequence 188. After termination of the exposure, the detector 22 may process the acquired data (e.g., image and offset data). In contrast to the imaging application in FIG. 5, the X-ray system 10 using the fluoroscopy imaging application possesses information to determine when the X-ray source 16 exposes X-ray radiation onto the detector 22 and when the imaging frames are changed from offset image frames 198 to imaging frames that include X-ray image data. As mentioned above, processing the offset data enables the calculation of an average offset image, which may be used along with the image data to subsequently generate an offset corrected image. The average offset image may be calculated without prior knowledge of the total number of offset image frames 198 sampled. As described in greater detail below, the techniques to average the total number of sampled offset image frames 198 significantly reduces the electronic noise. In certain embodiments, the average offset image may be calculated as each offset image frame 198 is acquired by the detector 22. Alternatively, the data (e.g., image and offset data) may be sent to the workstation or institution image review and storage system that may include HIS, RIS, and/or PACS for processing. As described in greater detail below, the techniques to average the total number of sampled offset image frames 198 significantly reduces the electronic noise.

As mentioned above, electronic noise presents a significant issue in generating images in imaging applications using low X-ray dosage (e.g., tomosynthesis and fluoroscopy imaging applications), particularly by introducing artifacts that may hinder the usefulness of the generated images. For example, assume that the electronic noise contained in each pixel value of the image is independent of each other with a zero mean and a standard deviation of a. After generating the offset corrected image using both the original image and offset data, the standard deviation of the electronic noise in the offset corrected image becomes $\sqrt{2}\sigma$. Thus, electronic noise for the offset corrected image is increased by 41.4% compared to the electronic noise of the original image.

The problem with electronic noise becomes further exacerbated when the detector 22 is without a priori knowledge of the beginning and ending times of an exposure as described above, and in which the X-ray image is formed by combining multiple imaging frames that include X-ray image data. For example, assuming the X-ray image is obtained by combining two imaging frames for a giving pixel $p_{i,j}$, the offset corrected pixel value is given by:

$$\hat{p}_{i,j} = p_{i,j}^{\{1\}} + p_{i,j}^{\{2\}} - 2O_{i,j}. \quad (1)$$

The mean and variance of the electronic noise are represented by $E\{\hat{p}_{i,j}\}$ and $E\{[\hat{p}_{i,j}]^2\}$, respectively, in the following formulas where:

$$E\{\hat{p}_{i,j}\} = E\{p_{i,j}^{\{1\}} + p_{i,j}^{\{2\}} - 2O_{i,j}\} = 0 \quad (2)$$

and $$E\{[\hat{p}_{i,j}]^2\} = E\{[p_{i,j}^{\{1\}}]^2 + [p_{i,j}^{\{2\}}]^2 + [2O_{i,j}]^2\} = (2+4)\sigma^2. \quad (3)$$

Since, as shown above, the electronic noise has zero mean and the 3 values $p_{i,j}^{\{1\}}$, $p_{i,j}^{\{2\}}$, and $O_{i,j}$ are independent of each other, the electronic noise of the X-ray image by combining N offset corrected images with the same offset becomes:

$$\sqrt{(N+N^2)\sigma^2} = \sqrt{1 + \frac{1}{N}} N\sigma \quad (4)$$

Thus, the standard deviation of the offset corrected image becomes $\sqrt{6}\cdot\sigma$ if the X-ray image is formed by combining 2 imaging frames that include X-ray image data, resulting in about 2.45 times the amount of electronic noise as compared to the original image. The problem with electronic noise may be further exacerbated when combining more than 2 imaging frames that include X-ray image data.

The imaging applications described above may generate many offset images that can be used for generating an average offset corrected to reduce the electronic noise in the offset corrected image. If we use the average of n offset image frames $\hat{o}_{i,j}^{\{n\}}$ (i.e., (i.e., the average offset image) obtained from the following equation:

$$\hat{o}_{i,j}^{\{n\}} = \frac{1}{n}\sum_{k=1}^{n} o_{i,j}(k) \quad (5)$$

where $\{o_{i,j}(k), k=1, 2, \ldots n\}$ represents the n offset image frames for offset correction, the mean of the electronic noise in the averaged image $\hat{o}_{i,j}^{\{n\}}$ is $$E\{\hat{o}_{i,j}^{\{n\}}\} = \frac{1}{n}\sum_{k=1}^{n} E\{o_{i,j}(k)\} = 0 \quad (6)$$

and the standard deviation of the electronic noise in the averaged image $\hat{o}_{i,j}^{\{n\}}$ becomes $$\sqrt{E\{\hat{o}_{i,j}^{\{n\}}\}^2} = \sqrt{\frac{1}{n^2}\sum_{k=1}^{n} E\{o_{i,j}(k)\}^2} = \frac{\sigma}{\sqrt{n}}. \quad (7)$$

However, in many imaging applications, the number of available offset images n is not known before the image acquisition. The number of available offset images depends on the specific timing in the workflow such as when the operator starts the X-ray exposure. If the number of available offset images is not known prior to image acquisition, then a recursive approach may be used to reconstruct the offset image for use in offset correction. Specifically equation (5) may be rewritten as follows:

$$\hat{o}_{i,j}^{\{n\}} = \frac{1}{n}\sum_{k=1}^{n} o_{i,j}(k) = \frac{1}{n}o_{i,j}(n) + \frac{n-1}{n}\cdot\frac{1}{n-1}\sum_{k=1}^{n-1} o_{i,j}(k) \quad (8)$$

to generate the following equation:

$$\hat{o}_{i,j}^{\{n\}} = \frac{1}{n}o_{i,j}(n) + \frac{n-1}{n}\hat{o}_{i,j}^{\{n-1\}}. \quad (9)$$

Equation 9 allows the average offset image to be constantly recalculated as each offset image frame is sampled to enable the use of the total number of offset image frames. As discussed in greater detail below, as the number of offset images frames used to calculate the average offset image increases, the electronic noise of the offset corrected image decreases.

Figure 8:
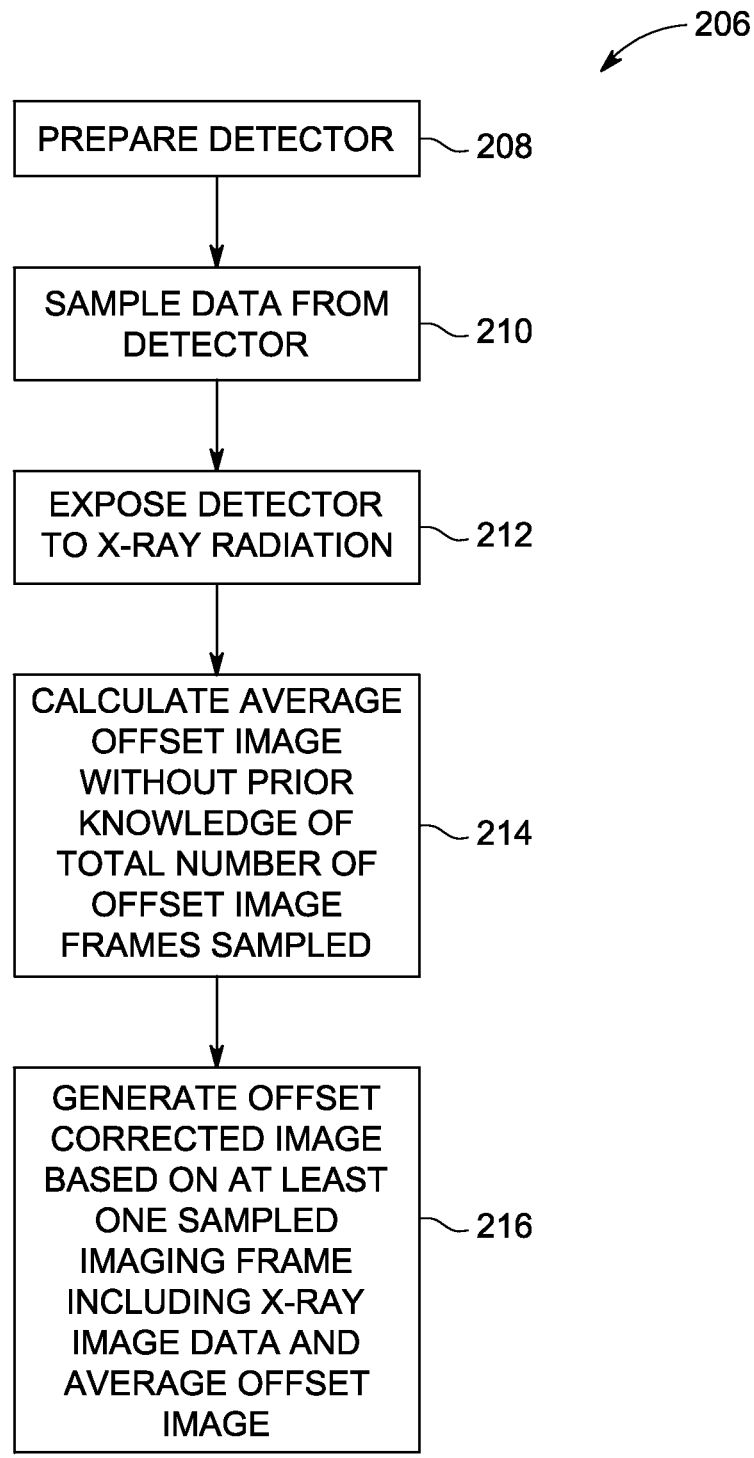
FIG. 8 is a flow diagram of a method for sampling data to calculate an average offset image and to generate an offset corrected image, in accordance with aspects of the present technique.
Figure 9:
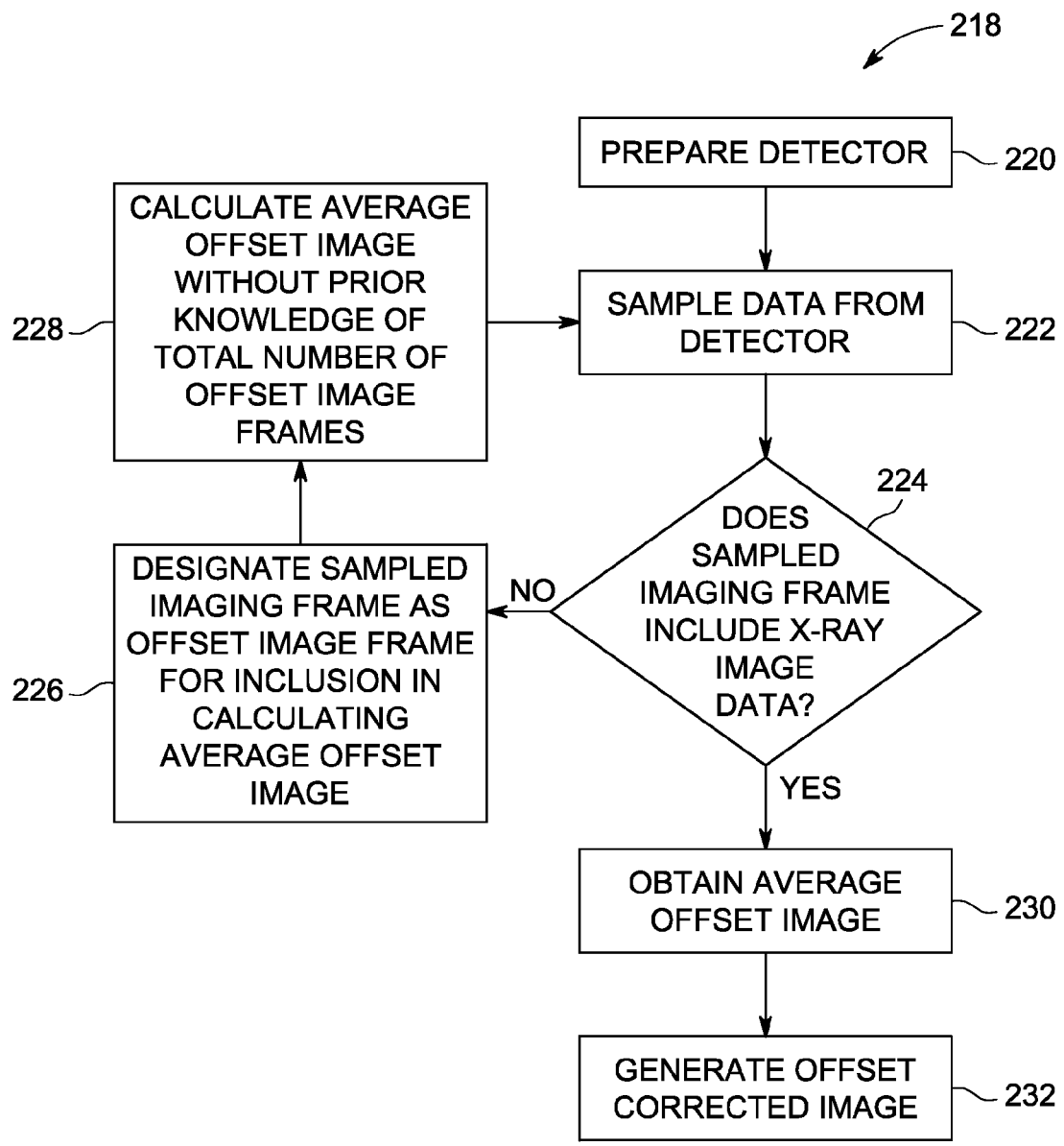
FIG. 9 is a flow diagram of method for sampling data and determining which data to use in calculating an average offset image and to generate an offset corrected image, in accordance with aspects of the present technique.

FIGS. 8 and 9 illustrate embodiments of techniques to generate offset images with minimal electronic noise. The following methods may be implemented by detector 22 and/or processing systems in communication with the detector 22 (e.g., detector control device 40, system controller, and/or institution image review and storage system). In particular, processing circuitry within the detector 22 or within a processing system separate from the detector 22 may be configured to calculate an average offset image without prior knowledge of a total number of offset image frames sampled. In particular, the processing circuitry may be configured to calculate the average offset image without prior knowledge of the total number of offset image frames as each offset frame is sampled. In addition, the processing circuitry may be configured to calculate the average offset image without prior knowledge of the total number of offset image frames subsequent to sampling the total number of offset image frames. Further, the processing circuitry may be configured to generate an offset corrected image based on at least one sampled imaging frame including X-ray image data and the average offset image.

FIG. 8 is a flow diagram of a method 206 for sampling data to calculate an average offset image and to generate an offset corrected image. The method 206 includes preparing the detector 22 (block 208). Preparation of the detector 22 (block 208) may include scrubbing the panel to reset the electronic circuitry. Preparation of the detector 22 (block 208) may also include sampling data (e.g., offset data) from the detector 22 (block 210). Sampling data (block 210) may include beginning to sample data (e.g., offset data) prior to and independently of initiation of an exposure. In addition, sampling of data (e.g., image data, block 210) may occur during and subsequent to the exposure. Following preparation of the detector 22 (blocks 208), the method 206 includes exposing the detector 22 to X-ray radiation via the X-ray radiation source 16 (block 212). During and after X-ray exposure (block 212), sampling of imaging frames that include X-ray image data occurs. In certain embodiments, after initiation of the exposure, sampling of X-ray image data occurs via the detector 22 without a priori knowledge of the beginning and ending times of the X-ray exposure (i.e., without communication of timing signals from the source controller).

From the sampled offset data (i.e., offset image frames), an average offset image is calculated without prior knowledge of the total number of offset image frames sampled (block 214). The average offset image is calculated from the total number of offset image frames sampled. Calculating the average offset image (block 214) may occur as each offset image is collected as described in greater detail below. In certain embodiments, calculating the average offset image (block 214) occurs subsequent to sampling the total number of offset image frames (e.g., post-processing by the host). By using the total number of offset image frames to calculate the average offset image, the electronic noise may be significantly reduced as compared to using some of the sampled offset image frames. After calculating the average offset image (block 214), one or more offset corrected images are generated based on at least one sampled imaging frame including X-ray image data and the average offset image (block 216). In embodiments, where the detector 22 is without a priori knowledge of the beginning and ending times of an exposure, the generated offset corrected image may be based on more than one sampling imaging frame that includes X-ray image data and the average offset image.

FIG. 9 is a flow diagram of a method 218 for sampling data and determining which data to use in calculating an average offset image and to generate an offset corrected image. Similar to method 206, the method 218 includes preparing the detector 22 (block 220). Preparation of the detector 22 (block 220) may include scrubbing the panel to reset the electronic circuitry. Preparation of the detector 22 (block 220) may also include sampling data (e.g., offset data) from the detector 22 (block 222). Sampling data (block 222) may include beginning to sample data (e.g., offset data) prior to and independently of initiation of an exposure. In addition, sampling of data (e.g., image data, block 222) may occur during and subsequent to the exposure.

As the detector 22 samples data (block 222), the method 218 includes determining as each imaging frame is sampled whether the imaging frame includes X-ray image data (block 224). If the sampled imaging frame does not include X-ray image data, the sampled imaging frame may be designated as an offset image frame for inclusion in calculating the average offset image (block 226). The method 218 includes using the designated offset image frame to calculate the average offset image without prior knowledge of the total number of offset image frames (block 228). In certain embodiments, calculating the average offset image without prior knowledge of the total number of offset image frames (block 228) occurs as each offset image is sampled using equation (9) as described above. Alternatively, calculating the average offset image without prior knowledge of the total number of offset image frames may subsequent to sampling the total number of offset image frames using equation (5) as described above. After designating the sampled imaging frame as an offset image frame (block 226), sampling of the data from the detector 22 (block 222) and determining whether the sampled imaging frame includes X-ray image data (block 224) continues. If the sampled imaging frame includes X-ray image data, then the calculated offset image (block 230) may be obtained. After obtaining the average offset image (block 230), one or more offset corrected images are generated based on at least one sampled imaging frame including X-ray image data and the average offset image (block 232). In embodiments, where the detector 22 is without a priori knowledge of the beginning and ending times of an exposure, the generated offset corrected image may be based on more than one sampling imaging frame that includes X-ray image data and the average offset image.

As mentioned above, as the number of offset images frames used to calculate the average offset image increases, the electronic noise of the offset corrected image decreases. Table 1 illustrates the ratio of the standard deviation of the electronic noise for a recursively reconstructed offset image (i.e., average offset image of total number of offset image frames) to the standard deviation of the electronic noise of the original offset image for a different number of offset image frames n given by $$\frac{1}{\sqrt{n}}.$$

As illustrated, as the number of offset image frames n used to generate the average offset image increases, the ratio of the standard deviation of the electronic noise for the average offset image to the standard deviation of the electronic noise of the original offset image decreases.

TABLE 1

| n | | | | |
|---|---|---|---|---|
| 5 | 10 | 20 | 40 | 80 |
| 44.7% | 31.6% | 22.4% | 15.8% | 11.2% |

As mentioned above, the electronic noise in the offset corrected image is increased by 41.4% compared to electronic noise in the original image. However, using the recursively reconstructed offset image reduces the electronic noise in the offset corrected image. Table 2 illustrates the change in electronic noise for an offset corrected image generated from a single imaging frame that includes X-ray image data (e.g., in a tomosynthesis or fluoroscopy application) and the average offset image for a different number of offset image frames n given by $$\left(\sqrt{1+\frac{1}{n}}\right)-1.$$

As illustrated, as the number of offset image frames n used to generate the average offset image increases, the increment of electronic noise in the offset corrected image decreases to as little as less than 1%.

TABLE 2

| n | | | | |
|---|---|---|---|---|
| 5 | 10 | 20 | 40 | 80 |
| 9.5% | 4.9% | 2.5% | 1.2% | 0.6% |

Table 2

The electronic noise in the offset corrected image is increased by 73.2% compared to electronic noise in the original image when two imaging frames that include X-ray image data are used in generating the offset corrected image. However, using the recursively reconstructed offset image also reduces the electronic noise in the offset corrected image when more than one imaging frame that includes X-ray image data is used to generate the offset corrected image. Table 3 illustrates the change in electronic noise for an offset corrected image generated from two imaging frames that include X-ray image data (e.g., in an imaging application where the detector 22 is without a priori knowledge of the beginning and ending times of an exposure) and the average offset image for a different number of offset image frames n given by $$\left(\sqrt{2 + \frac{1}{n}}\right) - 1.$$

As illustrated, as the number of offset image frames n used to generate the average offset image increases, the increment of electronic noise in the offset corrected image decreases to as little as less than 42%.

TABLE 3

| n | | | | |
|---|---|---|---|---|
| 5 | 10 | 20 | 40 | 80 |
| 48.3% | 44.9% | 43.2% | 42.3% | 41.9% |

Technical effects of the embodiments include providing methods and systems to reduce the electronic noise in offset corrected images generated by X-ray imaging systems. In particular, the X-ray imaging systems calculate an average offset image with reduced electronic noise using the total number of offset image frames sampled and without prior knowledge of the total number of offset image frames. Calculation of the average offset image may occur as each offset image frame is sampled. Alternatively, calculation of the average offset image may occur subsequent to sampling the total number of offset image frames. Using the average offset image of the total number of offset image frames generates an average offset image with minimal electronic noise, which in turn enables the generation of an offset corrected image with less electronic noise. Using the average offset image enables the reduction of electronic noise in imaging applications involving lower X-ray dosages as well as imaging applications where two or more imaging frames including X-ray imaging data are combined to generate the offset corrected image. As a result of these techniques the image quality from the digital X-ray detector 22 may be improved.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for processing X-ray image data, comprising:
exposing a digital detector to X-ray radiation;
sampling data via the digital detector including X-ray image data and offset image data, wherein the X-ray image data includes anatomical image data of a subject;
determining if a sampled imaging frame includes X-ray image data having anatomical image data;
designating the sampled imaging frame as an offset image frame for inclusion in calculating an average offset image if the sampled imaging frame does not include X-ray image data having anatomical image data; and
calculating the average offset image from one or more offset image frames without prior knowledge of a total number of offset image frames sampled if the sampled imaging frame includes X-ray image data having anatomical image data.

2. The method of claim 1, comprising preparing the detector by sampling data prior to exposing the digital detector to the X-ray radiation.

3. The method of claim 2, wherein preparing the detector comprises beginning sampling data prior to and independent of exposing the digital detector to the X-ray radiation.

4. The method of claim 1, wherein calculating the average offset image without prior knowledge of the total number of offset image frames occurs as each offset image frame is designated.

5. The method of claim 1, wherein calculating the average offset image without prior knowledge of the total number of offset image frames occurs subsequent to sampling the total number of offset image frames.

6. The method of claim 1, comprising generating an offset corrected image based on at least one sampled imaging frame including X-ray image data having anatomical image data and the average offset image.

7. The method of claim 1, wherein the digital detector is configured to calculate the average offset image.

8. The method of claim 1, wherein a processing system in communication with the detector is configured to calculate the average offset image.

9. A method for processing X-ray image data, comprising:
sampling data via a digital detector including X-ray image data and offset image data, wherein the X-ray image data includes anatomical image data of a subject and the offset image data does not include anatomical image data of the subject;
determining if sampled imaging frames include X-ray image data having anatomical image data; and
calculating an average offset image from one or more offset image frames of the offset image data without prior knowledge of a total number of offset image frames sampled if a sampled imaging frame includes X-ray image data having anatomical image data.

10. The method of claim, 9 comprising designating sampled imaging frames as offset image frames for inclusion in calculating the average offset image if the sampled imaging frames do not include X-ray image data having anatomical image data.

11. The method of claim 9, comprising generating an offset correct image based on at least one sampled imaging frame including X-ray image data having anatomical image data and the average offset image.

12. The method of claim 9, comprising preparing the detector by sampling data prior to exposing the digital detector to X-ray radiation.

13. The method of claim 10, wherein preparing the detector comprises beginning sampling data prior to and independent of exposing the digital detector to the X-ray radiation.

14. The method of claim 9, wherein calculating the average offset image without prior knowledge of the total number of offset image frames occurs as each offset image frame is sampled.

15. The method of claim 9, wherein calculating the average offset corrected image without prior knowledge of the total number of offset image frames occurs subsequent to sampling the total number of offset image frames.

16. An X-ray imaging system, comprising:
an X-ray radiation source;
a digital detector configured to receive X-ray radiation from the source and to sample data including X-ray image data and offset image data, wherein the X-ray image data includes anatomical image data of a subject; and
processing circuitry configured to:
    determine if a sampled imaging frame includes X-ray image data having anatomical image data;
    designate the sampled imaging frame as an offset image frame for inclusion in calculating an average offset image if the sampled imaging frame does not include X-ray image data having anatomical image data; and
    calculate the average offset image from one or more offset image frames without prior knowledge of a total number of offset image frames sampled if the sampled imaging frame includes X-ray image data having anatomical image data.

17. The system of claim 16, wherein the detector comprises the processing circuitry.

18. The system of claim 17, wherein a processing system separate from the digital detector and in communication with the digital detector comprises the processing circuitry.

19. The system of claim 16, wherein the processing circuitry is configured to calculate the average offset image without prior knowledge of the total number of offset image frames as each offset image frame is designated.

20. The system of claim 16, wherein the processing circuitry is configured to calculate the average offset image without prior knowledge of the total number of offset image frames subsequent to sampling the total number of offset image frames.

21. The system of claim 16, wherein the processing circuitry is configured to generate an offset corrected image based on at least one sampled imaging frame including X-ray image data having anatomical image data and the average offset image.

* * * * *